United States Patent [19]

Clough et al.

[11] Patent Number: 4,883,807
[45] Date of Patent: Nov. 28, 1989

[54] 1,2,5,6-TETRAHYDROPYRIDYL TRIAZOLES AND TETRAZOLES USEFUL AS FUNGICIDES

[75] Inventors: John M. Clough, Marlow; Christopher R. A. Godfrey, Bracknell; Paul J. de Fraine, Wokingham; Brian K. Snell, Reading, all of England

[73] Assignee: Imperial Chemical Industries PLC, London, United Kingdom

[21] Appl. No.: 127,769

[22] Filed: Dec. 1, 1987

[30] Foreign Application Priority Data

Dec. 16, 1986 [GB] United Kingdom ............... 8630027
Mar. 24, 1987 [GB] United Kingdom ............... 8706950

[51] Int. Cl.$^4$ .................. A61K 31/40; C07D 207/50; C07D 207/337
[52] U.S. Cl. .................................. 514/427; 548/558; 548/561; 514/427
[58] Field of Search ............... 514/426, 427; 548/558, 548/561, 562

[56] References Cited

FOREIGN PATENT DOCUMENTS

| | | |
|---|---|---|
| 0084236 | 7/1983 | European Pat. Off. |
| 0147870 | 7/1985 | European Pat. Off. |
| 0150499 | 8/1985 | European Pat. Off. |
| 0174088 | 3/1986 | European Pat. Off. |
| 0206523 | 12/1986 | European Pat. Off. |
| 2821639 | 11/1979 | Fed. Rep. of Germany. |
| 3019044 | 11/1981 | Fed. Rep. of Germany. |
| 3217094 | 11/1983 | Fed. Rep. of Germany. |
| 3514116 | 10/1986 | Fed. Rep. of Germany. |
| 967135 | 9/1965 | France .......................... 514/235.5 |
| 2149403 | 6/1985 | United Kingdom. |

OTHER PUBLICATIONS

Maier et al, *Angewandte Chemie Int. Ed. Engl.*, 21(7):546–7 (1982).
Yang et al., *The Journal of Organic Chemistry*, 44:4160–4164 (1979).
Jones et al., *Tetrahedron*, 24(3):2013–2017 (Feb. 3, 1968).
White et al., *The Journal of Organic Chemistry*, 42:4248–4251 (1977).
Jefford et al., *Helvetica Chimica Acta*, 66:2666–2671 (1983).
Lin et al., *The Journal of Organic Chemistry*, 44: pp. 4160–4164 (1979).
*Chemical Abstracts*, vol. 90, No. 87 469q (1977); Thomas et al.
*Chemical Abstracts*, vol. 90, No. 31 904k (1977); Quaglia.
*Chemical Abstracts*, vol. 87, No. 5 985f (1977); Balasubramanyan.
*Agnew. Chem. Int. Ed. Engl.*, 94(7): pp. 546–547 (1982); Maier et al.
*Chemical Abstracts*, vol. 89, No. 146861r (1978); Sloane et al.
*Chemical Abstracts*, vol. 86, No. 106993s (1977); Maier et al.
*Chemical Abstracts*, vol. 83, No. 195250a (1975); Furutachi et al.
*Chemical Abstracts*, vol. 77, No. 126510z (1972); Hoffmann et al.
C.A., 97:72305d; Maier et al. (1982).

Primary Examiner—Mary C. Lee
Assistant Examiner—E. Brendan Magrab
Attorney, Agent, or Firm—Cushman, Darby & Cushman

[57] ABSTRACT

Compounds of the formula (I):

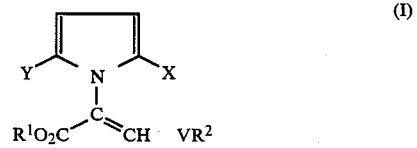

and stereoisomers and salts thereof, wherein $R^1$ and $R^2$, are optionally substituted alkyl; V is either oxygen or sulphur; Y is hydrogen, optionally substituted alkyl, cyano, nitro or halogen; X is

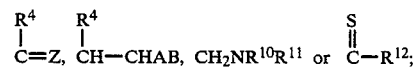

Z is $NOR^5$ or

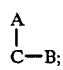

A is $CO_2R^6$, $COR^7$, cyano, nitro or acylamino; B is hydrogen, optionally substituted alkyl, optionally substituted aryl, $CO_2R^8$, $COR^9$, cyano, nitro or acylamino, or A and B together form a ring containing one or more heteroatoms; $R^4$ is $CO_2R^3$ or $R^{17}$; $R^{12}$ is $OR^{13}$, $SR^{14}$, $NR^{15}R^{16}$ or $R^{18}$; $R^3$ is optionally substituted alkyl; and $R^5$ to $R^{11}$ and $R^{13}$ to $R^{18}$, which are the same or different, are hydrogen, optionally substituted alkyl, optionally substituted cycloalkyl, optionally substituted cycloalkylalkyl, optionally substituted alkenyl, optionally substituted alkynyl, optionally substituted aralkyl, optionally substituted aryl, or optionally substituted heteroaryl, or $R^{10}$ and $R^{11}$, or $R^{15}$ and $R^{16}$ together with their adjacent nitrogen atom join to form a saturated ring (except that $R^{10}$ and $R^{11}$, together with their adjacent nitrogen atom, do not form an unsubstituted piperidine ring when $R^1$ and $R^2$ are both methyl, Y is hydrogen and V is oxygen) optionally containing one or more hetero atoms in addition to the nitrogen atom, for example, a pyrrolidine or morpholine. These compounds are useful in agriculture, for example, as fungicides or plant growth regulators.

4 Claims, No Drawings

1,2,5,6-TETRAHYDROPYRIDYL TRIAZOLES AND TETRAZOLES USEFUL AS FUNGICIDES

This invention relates to derivatives of acrylic acid useful in agriculture (especially as fungicides but also as plant growth regulators, insecticides, nematocides and miticides), to processes for preparing them, to agricultural (especially fungicidal) compositions containing them, and to methods of using them to combat fungi (especially fungal infections in plants), to regulate plant growth and to control or kill insects, nematodes and mites.

The invention provides a compound having the general formula (I):

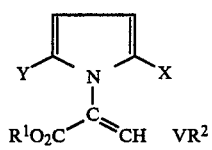

(I)

and stereoisomers and salts thereof, wherein $R^1$ and $R^2$, which are the same or different, are optionally substituted alkyl (preferably methyl); V is either oxygen or sulphur; Y is hydrogen, optionally substituted alkyl, cyano, nitro or halogen (fluorine, chlorine, bromine, or iodine); X is

$$C=Z, \quad CH-CHAB, \quad CH_2NR^{10}R^{11} \quad or \quad \overset{S}{\underset{\|}{C}}-R^{12};$$

Z is $NOR^5$ or

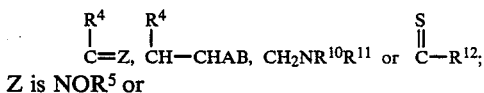

A is $CO_2R^6$, $COR^7$, cyano, nitro or acylamino; B is hydrogen, optionally substituted alkyl, optionally substituted aryl, $CO_2R^8$, $COR^9$, cyano, nitro or acylamino, or A and B together form a ring containing one or more heteroatoms; $R^4$ is $CO_2R^3$ or $R^{17}$; $R^{12}$ is $OR^{13}$, $SR^{14}$, $NR^{15}R^{16}$ or $R^{18}$; $R^3$ is optionally substituted alkyl; and $R^5$ to $R^{11}$ and $R^{13}$ to $R^{18}$, which are the same or different, are hydrogen, optionally substituted alkyl, optionally substituted cycloalkyl, optionally substituted cycloalkylalkyl, optionally substituted alkenyl, optionally substituted alkynyl, optionally substituted aralkyl, optionally substituted aryl, or optionally substituted heteroaryl, or $R^{10}$ and $R^{11}$, or $R^{15}$ and $R^{16}$ together with their adjacent nitrogen atom join to form a saturated ring (except that $R^{10}$ and $R^{11}$, together with their adjacent nitrogen atom, do not form an unsubstituted piperidine ring when $R^1$ and $R^2$ are both methyl, Y is hydrogen and V is oxygen) optionally containing one or more hetero atoms in addition to the nitrogen atom, for example, a pyrrolidine or morpholine ring.

The compounds of the invention contain at least one carbon-carbon double bond and are sometimes obtained as mixtures of geometric isomers. However, these mixtures can be separated into individual isomers, and this invention embraces such isomers and mixtures thereof in all proportions including those which consist substantially of the (E)-isomer and those which consist substantially of the (Z)-isomer.

The individual isomers which result from the unsymmetrically substituted double bond of the acrylate group are identified by the commonly used terms "E" and "Z". These terms are defined according to the Cahn-Ingold-Prelog system which is fully described in the literature (see, for example, J March, "Advanced Organic Chemistry", 3rd edition, Wiley-Interscience, page 109 et seq).

Usually one isomer is more fungicidally active than the other; the more active isomer being the one in which the group $-VR^2$ is on the same side of the double bond as the pyrrole ring. In the case of the compounds of the present invention this is the (Z)-isomer. The (Z)-isomers form a preferred embodiment of the invention.

The formula:

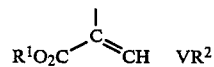

used herein indicates that the compound may be in the form of one or both isomers, i.e.

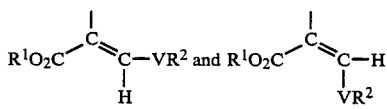

Compounds in which X is $CH_2NR^{10}R^{11}$ can form acid addition salts, for example hydrochloride salts and hydrosulphate salts. They can also form quaternary ammonium salts, for example the methiodide salt or the benzyl halide (e.g. bromide) quaternary ammonium salt.

Preferred alkyl groups contain from 1 to 6, especially 1 to 4, carbon atoms and can be in the form of straight or branched chains; they include methyl, ethyl, propyl (n- and iso-propyl) and butyl (n-, sec-, iso-, and tert-butyl).

It is preferred that $R^1$ and $R^2$ are both methyl.

Preferred cycloalkyl groups are those containing from 3 to 6 carbon atoms, i.e. cyclopropyl, cyclobutyl, cyclopentyl, and cyclohexyl. Preferred cycloalkylalkyl groups are those containing from 3 to 8, especially 3 to 6, carbon atoms in the alkyl ring and 1 to 6, especially 1 to 4, carbon atoms in the attached alkyl chain. Examples are cyclopropylethyl and cyclohexylmethyl.

Optional substituents of alkyl, cycloalkyl and cycloalkylalkyl include hydroxy, halogen (especially chlorine and fluorine), $C_{1-4}$ alkoxy and $C_{1-4}$ alkoxycarbonyl.

A preferred aryl group is phenyl which may be unsubstituted or substituted with, for example, 1, 2 or 3 substituents at the 2-, 3- or 4-positions of the ring. Optional substituents carried by the aryl group include halogen (especially chlorine or fluorine), hydroxy, alkyl, trifluoromethyl, and trifluoromethoxy and may be the same or different. Examples of optionally substituted aryl groups are phenyl, 2-, 3- or 4-chlorophenyl, 2,4- or 3,5-dichlorophenyl, 2,4- or 3,5-difluorophenyl, 2-, 3- or 4-fluorophenyl, 2-, 3- or 4-methoxyphenyl, 2,4-dimethoxyphenyl, 2-fluoro-4-chlorophenyl, 2-, 3- or 4-methylphenyl and 2-, 3- or 4-trifluoromethylphenyl.

Aralkyl includes, particularly, phenyl($C_{1-4}$)alkyl (especially benzyl, phenylethyl and phenylpropyl) and the aryl moiety may be substituted in the same way as the aryl groups above.

Alkenyl and alkynyl groups preferably contain 2 to 6, more preferably 2 to 4, carbon atoms in the form of straight or branched chains. Allyl and propargyl are examples. Optional substituents of alkenyl and alkynyl include aromatic and heteroaromatic groups (such as phenyl, furyl, thienyl and pyridyl) which may themselves be substituted in the same way as the aryl groups above.

Heteroaryl includes pyridyl, pyrimidinyl, thiophenyl, furyl and pyrroyl. Optional substituents include those described for the aryl groups above.

In one particular aspect, the invention provides compounds having the formula (Ia):

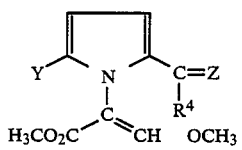
(Ia)

and stereoisomers thereof, wherein Y is hydrogen, optionally substituted alkyl, cyano, nitro or halogen; $R^4$ is hydrogen, optionally substituted alkyl, or optionally substituted aryl; Z is $NOR^5$ or

$R^5$ is hydrogen, optionally substituted alkyl, optionally substituted alkenyl, optionally substituted alkynyl, optionally substituted aralkyl, optionally substituted aryl, or optionally substituted heteroaryl; A is $CO_2R^6$, $COR^7$, cyano, nitro, or acylamino; B is hydrogen, optionally substituted alkyl, optionally substituted aryl, $CO_2R^8$, $COR^9$, cyano, nitro or acylamino, or A and B together form a ring containing one or more heteroatoms; and $R^6$, $R^7$, $R^8$ and $R^9$, which are the same or different, are optionally substituted alkyl, optionally substituted cycloalkyl, optionally substituted cycloalkylalkyl, optionally substituted alkenyl, optionally substituted alkynyl, optionally substituted aralkyl, optionally substituted aryl, or optionally substituted heteroaryl. Preferred alkyl, alkenyl, alkynyl, aralkyl, aryl and heteroaryl groups and their optional substituents are the same as those described above.

The invention is illustrated by the compounds listed in Tables I to III which follow.

NMR data for selected compounds are given in Table IV.

TABLE I

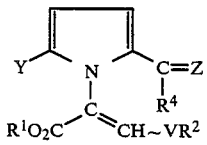

| COMPOUND NO. | $R^1$ | $R^2$ | $R^4$ | V | Y | Z | Mpt. °C. | OLEFINIC* | ISOMER+ | ISOMER° |
|---|---|---|---|---|---|---|---|---|---|---|
| 1 | $CH_3$ | CH | H | O | H | $NOCH_3$ | Oil | 7.57 | Z | E |
| 2 | $CH_3$ | $CH_3$ | H | O | H | $NOCH_3$ | Oil | 7.60 | Z | Z |
| 3 | $CH_3$ | $CH_3$ | H | O | H | $NOCH_2CH=CH_2$ | Oil | 7.50 | Z | E |
| 4 | $CH_3$ | $CH_3$ | H | O | H | $NOCH_2CH=CH_2$ | Oil | 7.68 | Z | Z |
| 5 | $CH_3$ | $CH_3$ | H | O | H | $NOCH_2C_6H_5$ | Oil | 7.44 | Z | E |
| 6 | $CH_3$ | $CH_3$ | H | O | H | $NOCH_2C_6H_5$ | | | Z | Z |
| 7 | $CH_3$ | $CH_3$ | H | O | H | $NOCH_2C\equiv CH$ | Oil | 7.53 | Z | E |
| 8 | $CH_3$ | $CH_3$ | H | O | H | $NOCH_2C\equiv CH$ | | | Z | Z |
| 9 | $CH_3$ | $CH_3$ | $CH_3$ | O | H | $NOCH_3$ | | | Z | E |
| 10 | $CH_3$ | $CH_3$ | $CH_3$ | O | H | $NOCH_3$ | | | Z | Z |
| 11 | $CH_3$ | $CH_3$ | H | O | H | $CHCO_2CH_3$ | Oil | 7.70 | Z | E |
| 12 | $CH_3$ | $CH_3$ | H | O | H | $CHCO_2C_2H_5$ | Oil | 7.68 | Z | E |
| 13 | $CH_3$ | $CH_3$ | H | O | H | NOH | | | Z | E |
| 14 | $CH_3$ | $CH_3$ | $C_6H_5$ | O | H | $NOCH_3$ | | | Z | E |
| 15 | $CH_3$ | $CH_3$ | $C_6H_5$ | O | H | NOH | | | Z | E |
| 16 | $CH_3$ | $CH_3$ | $CH_3$ | O | H | $NOC_6H_5$ | | | Z | E |
| 17 | $CH_3$ | $CH_3$ | $CH_3$ | O | H | $NO(3-F-C_6H_4)$ | | | Z | E |
| 18 | $CH_3$ | $CH_3$ | $CO_2CH_3$ | O | H | $NOCH_3$ | | | Z | E |
| 19 | $CH_3$ | $CH_3$ | H | O | H | C(CN)(CO_2C_2H_5) | 121-2 | 7.76 | Z | E |
| 20 | $CH_3$ | $CH_3$ | H | O | H | $CHCOCH_3$ | | | Z | E |
| 21 | $CH_3$ | $CH_3$ | H | O | H | $CHCOC_6H_5$ | | | Z | E |
| 22 | $CH_3$ | $CH_3$ | H | O | H | $C(CH_3)CO_2C_2H_5$ | | | Z | E |
| 23 | $CH_3$ | $CH_3$ | H | O | H | $C(CH_3)NO_2$ | | | Z | E |
| 24 | $CH_3$ | $CH_3$ | H | O | $CH_3$ | $NOCH_2CH=CH_2$ | | | Z | E |

*Chemical shift of singlet from olefinic proton on the beta-alkoxyacrylate or beta-(alkylthio)acrylate group (ppm from tetramethylsilane). Solvent:$CDCl_3$.
+Geometry of beta-alkoxyacrylate or beta-(alkylthio)acrylate group.
°Geometry of oxime, oxime ether, or olefin, at the 2-position of the pyrrole.

TABLE II

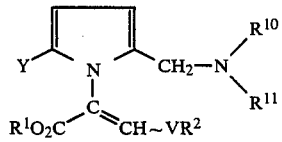

| COMPOUND NO. | $R^1$ | $R^2$ | V | Y | $R^{10}$ | $R^{11}$ | Mpt. °C. | OLEFINIC* | ISOMER+ | QUATERNARY SALT |
|---|---|---|---|---|---|---|---|---|---|---|
| 1 | $CH_3$ | $CH_3$ | O | H | $CH_3$ | $CH_3$ | 54–6 | 7.47 | Z | — |
| 2 | $CH_3$ | $CH_3$ | O | H | $CH_3$ | $CH_3$ | ca.300 DECOMP. | 8.01 | Z | METHIODIDE SALT |
| 3 | $CH_3$ | $CH_3$ | O | H | H | $C_6H_5$ | | | Z | — |
| 4 | $CH_3$ | $CH_3$ | O | H | H | $\underline{n}$-$C_3H_7$ | | | Z | — |
| 5 | $CH_3$ | $CH_3$ | O | H | —$CH_2CH_2OCH_2CH_2$— | | Oil | 7.54 | Z | — |
| 6 | $CH_3$ | $CH_3$ | O | H | $CH_3$ | $C_6H_5$ | | | Z | — |
| 7 | $CH_3$ | $CH_3$ | O | $CH_3$ | $CH_3$ | $CH_3$ | | | Z | — |
| 8 | $CH_3$ | $CH_3$ | O | H | $C_2H_5$ | $C_2H_5$ | | | Z | — |

*Chemical shift of singlet from olefinic proton on the beta-alkoxyacrylate or beta-(alkylthio)acrylate group (ppm from tetramethylsilane). Solvent:CDCl$_3$.
+Geometry of beta-alkoxyacrylate or beta-(alkylthio)acrylate group.

TABLE III

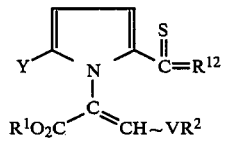

| COMPOUND NO. | $R^1$ | $R^2$ | V | Y | $R^{12}$ | Mpt. °C. | OLEFINIC* | ISOMER+ |
|---|---|---|---|---|---|---|---|---|
| 1 | $CH_3$ | $CH_3$ | O | H | $C_6H_5$ | | | Z |
| 2 | $CH_3$ | $CH_3$ | O | H | 4-Cl—$C_6H_4$ | | | Z |
| 3 | $CH_3$ | $CH_3$ | O | H | 3-Cl—$C_6H_4$ | | | Z |
| 4 | $CH_3$ | $CH_3$ | O | H | 4-F—$C_6H_4$ | | | Z |
| 5 | $CH_3$ | $CH_3$ | O | H | 2-F—$C_6H_4$ | | | Z |
| 6 | $CH_3$ | $CH_3$ | O | H | 3-$CH_3$—$C_6H_4$ | | | Z |
| 7 | $CH_3$ | $CH_3$ | O | H | 3-$CH_3O$—$C_6H_4$ | | | Z |
| 8 | $CH_3$ | $CH_3$ | O | H | 3,5-Di—F—$C_6H_3$ | | | Z |
| 9 | $CH_3$ | $CH_3$ | O | H | 3,5-Di—$CH_3$—$C_6H_3$ | | | Z |
| 10 | $CH_3$ | $CH_3$ | O | H | 3,5-Di—Cl—$C_6H_3$ | | | Z |
| 11 | $CH_3$ | $CH_3$ | O | H | O($\underline{n}$-$C_3H_7$) | | | Z |
| 12 | $CH_3$ | $CH_3$ | O | H | $OC_6H_5$ | | | Z |
| 13 | $CH_3$ | $CH_3$ | O | H | O($\underline{n}$-$C_4H_9$) | | | Z |
| 14 | $CH_3$ | $CH_3$ | O | H | (NH$CH_3$) | | | Z |
| 15 | $CH_3$ | $CH_3$ | O | H | N($CH_3$)$_2$ | | | Z |
| 16 | $CH_3$ | $CH_3$ | O | H | NH$C_6H_5$ | | | Z |
| 17 | $CH_3$ | $CH_3$ | O | H | N($CH_3$)$C_6H_5$ | | | Z |
| 18 | $CH_3$ | $CH_3$ | O | H | $SCH_3$ | | | Z |
| 19 | $CH_3$ | $CH_3$ | O | H | $SC_6H_5$ | | | Z |
| 20 | $CH_3$ | $CH_3$ | O | H | $NHCO_2C_2H_5$ | | | Z |
| 21 | $CH_3$ | $CH_3$ | O | H | NH(3-F—$C_6H_4$) | | | Z |
| 22 | $CH_3$ | $CH_3$ | O | H | NH(4-Cl—$C_6H_4$) | | | Z |

*Chemical shift of singlet from olefinic proton on the beta-alkoxyacrylate or beta-(alkylthio)acrylate group (ppm from tetramethylsilane). Solvent:CDCl$_3$.
+Geometry of beta-alkoxyacrylate or beta-(alkylthio)acrylate group.

TABLE IV

Selected proton NMR data

Table IV shows selected proton NMR data for certain compounds described in Tables I and II. Chemical shifts are measured in ppm from tetramethylsilane, and deuterochloroform was used as solvent throughout. The following abbreviations are used:

| | | | |
|---|---|---|---|
| br | = broad | t = triplet | ppm = parts per million |
| s | = singlet | q = quartet | J = coupling constant in hertz (Hz) |
| d | = doublet | m = multiplet | |

| COMPOUND NO. | TABLE NO. | NMR DATA |
|---|---|---|
| 1 | I | 3.75 (3) s, 3.87 (3) s, 3.89 (3) s, 6.3 (1) m, 6.6 (2) m, 7.57 (1) s, 7.88 (1) s. |
| 2 | I | 3.64 (3) s, 3.80 (3) s, 3.90 (3) s, 6.3 (1) m, 6.5 (1) m, 6.90 (1) s, 7.1 (1) m, 7.60 (1) s. |
| 3 | I | 3.70 (3) s, 3.84 (3) s, 4.5 (2) m, 5.1–5.4 (2) m, 5.8–6.7 (4) m, 7.50 (1) s, 7.88 (1) s. |
| 4 | I | 3.72 (3) s, 3.88 (3) s, 4.7 (2) m, 5.1–6.7 (5) m, 7.03 (1) s, 7.3 (1) m, 7.68 (1) s. |
| 5 | I | 3.64 (3) s, 3.72 (3) s, 5.06 (2) s, 6.2–6.7 (3) m, 7.2–7.4 (5) m, 7.44 (1) s, 7.92 (1) s. |
| 7 | I | 3.73 (3) s, 3.88 (3) s, 4.64 (2) s, 6.3–6.7 (3) m, 7.53 (1) s, 7.90 (1) s. |
| 11 | I | 3.76 (6) s, 3.90 (3) s, 6.1 (1) d (J = 16Hz), 6.4 (1) m, 6.8 (2) m, 7.4 (1) d (J = 16Hz), 7.70 (1) s. |
| 12 | I | 1.3 (3) t, 3.75 (3) s, 3.86 (3) s, 4.2 (2) q, 6.1 (1) d (J = 16Hz), 6.2–6.8 (3) m, 7.3 (1) d (J = 16Hz), 7.68 (1) s. |

TABLE IV-continued

| 19 | I  | 3.75 (3) s, 3.81 (3) s, 6.46 (1) m, 6.76 (1) m, 7.06 (1) s, 7.2–7.6 (6) m, 7.76 (1) s. |
|----|----|---|
| 1  | II | 2.08 (6) s, 3.16 (2) s, 3.64 (3) s, 3.80 (3) s, 6.0–6.2 (2) m, 6.4–6.5 (1) m, 7.47 (1) s. |
| 2  | II | 3.00 (6) s, 3.78 (3) s, 3.96 (3) s, 4.30 (2) s, 6.4 (1) m, 6.6 (1) m, 6.8 (1) m, 8.01 (1) s. |
| 5  | II | 2.2–2.4 (4) m, 3.3 (2) m, 3.5–3.6 (4) m, 3.73 (3) s, 3.86 (3) s, 6.1 (1) m, 6.17 (1) m, 6.53 (1) m, 7.54 (1) s. |

The compounds of the invention having the general formula (I), in which V is oxygen, can be prepared by the steps shown in Schemes I to III. Throughout the Schemes the terms A, B, $R^1$ to $R^{18}$, X, Y and Z are as defined above and L is a leaving group such as a halide (iodide, bromide or, especially, chloride) or $-R^2SO_4$ anion.

Referring to Scheme I, compounds of the invention having the general formula (I) wherein X is

and Z is $NOR^5$ [compound (IA) of Scheme I] may be prepared from substituted pyrroles of general formula (II) by treatment with amines of general formula $H_2NOR^5$ in a suitable solvent such as methanol.

Compounds of the general formula (I) wherein X is

and Z is CAB [compound (IB) of Scheme I] may be prepared from substituted pyrroles of general formula (II) by treatment with a Wittig reagent of general formula $(C_6H_5)_3P{:}CAB$, (see, for example, "The Chemistry of Pyrroles", Academic Press, R. A. Jones, G. P. Bean, page 316, and references therein). Alternatively, when one or both of the groups A and B stabilise an adjacent negative charge, compounds (IB) of Scheme I may be prepared by condensation of substituted pyrroles of general formula (II) with compounds of general formula $CH_2AB$. They may also be prepared by reaction of compounds of general formula (III) of Scheme I with compounds of general formula $R^4C{=}C-A$, optionally in the presence of a Lewis acid; in this case the group B of the product (1B) is hydrogen (see, for example, "Advances in Heterocyclic Chemistry", Academic Press, 1978, 23, 286 and references therein).

Compounds of general formula (I) wherein X is

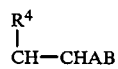

[compound (IC) of Scheme I] may be prepared by catalytic hydrogenation (preferably using a palladium catalyst) of compounds of general formula (IB) of Scheme I. Alternatively, they may be prepared from substituted pyrroles of general formula (III) by treatment with compounds of general formula

optionally in the presence of a Lewis acid (see D. O. Cheng, T. L. Bowman and E. LeGoff, *Journal of Heterocyclic Chemistry*, 1976, 13, 1145).

Compounds of the general formula (I) wherein X is $CH_2NR^{10}R^{11}$ [compound (ID) of Scheme I] may be prepared from substituted pyrroles of general formula (III) of Scheme I by treatment with an amine of general formula $HNR^{10}R^{11}$ and formaldehyde using a Mannich reaction (see W. Hertz and J. L. Rogers, *J. Amer. Chem. Soc.*, 1951, 73, 4921).

Scheme I

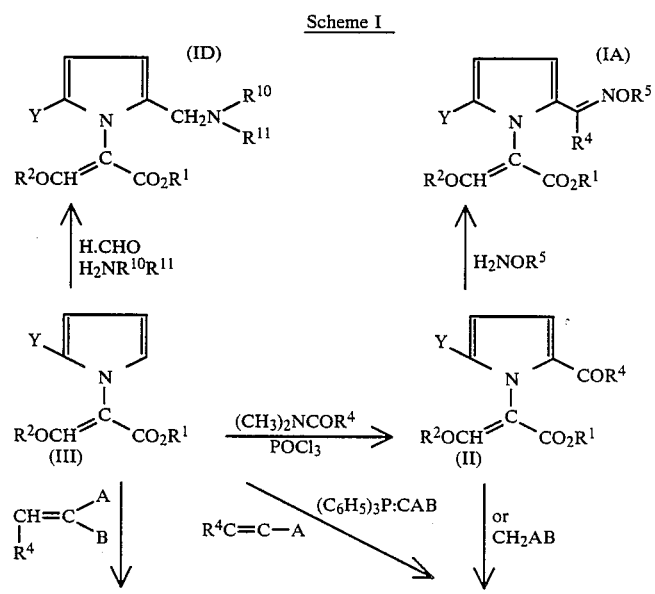

Scheme I -continued

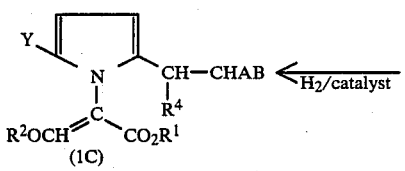 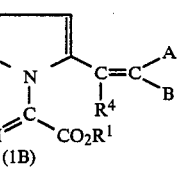 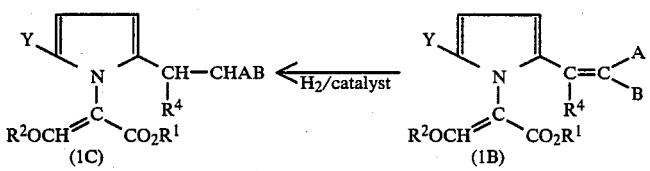

Compounds of the general formula (II) of Scheme I may be prepared from substituted pyrroles of general formula (III) by treatment with a Vilsmeier reagent, and subsequent quenching with an aqueous base. The Vilsmeier reagent may, for example, be prepared by adding phosphoryl chloride to an amide of general formula $(CH_3)_2NCOR^4$ (see for example, *Organic Synthesis*, John Wiley and Sons, Inc., Collective Volume 4, page 831, and references therein).

Referring to Scheme II, compounds of the general formula (I) wherein X is

[Compound (IE) of Scheme II] may be prepared from substituted pyrroles of general formula (III), by treatment with a compound of general formula

optionally in the presence of a Lewis acid catalyst.

Alternatively, when $R^{12}$ is $NHR^{15}$, they may be prepared by treatment of substituted pyrroles of general formula (III) with an isothiocyanate of general formula $R^{15}$—NCS, optionally in the presence of a Lewis acid catalyst (see, for example, V Looney-Dean, B. S. Lindamood and E. P. Papadopoulos, *Synthesis*, 1984, 68 and references therein). Compounds of formula (IE) wherein $R^{12}$ is $R^{18}$ may be prepared via the Vilsmeier complex of general formula (IV); treatment of substituted pyrroles of general formula (III) with an amide of general formula $(CH_3)_2NCOR^{18}$ in phosphoryl chloride generates a Vilsmeier complex which is then quenched with the group $-SH$, to give the thioaroylpyrroles of general formula (IE) [see, for example, T. Anderson, M. Phil. Thesis, University of East Anglia, 1971].

Scheme II

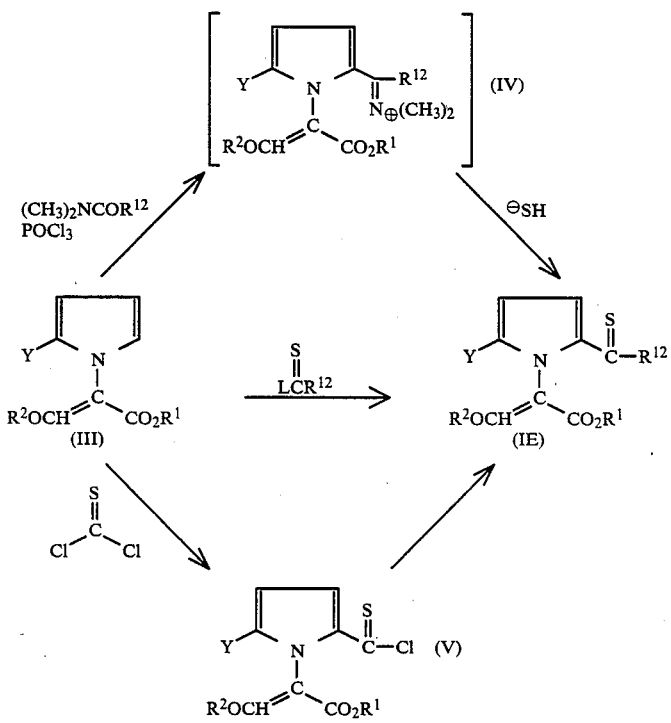

Alternatively, if compounds of general formula (III) are treated with thiophosgene ($CSCl_2$) the intermediate of general formula (V) is obtained; this may then be transformed into compounds of general formula (IE) by methods known in the chemical literature. Examples include treatment with amines of general formula $HNR^{15}R^{16}$, or alcohols of general formula $HOR^{13}$ to give compounds where $R^{12}$ is the group $NR^{15}R^{16}$ and $OR^{13}$ respectively (see for example, P. S. Clezy, G. A. Smythe, *Australian Journal of Chem.*, 1969, 22, 239).

Referring to Scheme III, compounds of general formula (III) can be prepared by treatment of substituted acetic esters of general formula (VII) of Scheme III with a base and a formic ester $HCO_2R^1$, such as methyl formate, in a suitable solvent and quenching the reaction with a suitable species of general formula $R^2L$.

Alternatively, compounds of general formula (VI) may be isolated by quenching the reaction with acid. In such cases, conversion into compounds of general formula (III) can be performed in a separate step by successive treatments with a suitable base (such as sodium carbonate or potassium carbonate) and a suitable reagent of general formula $R^2L$ in a suitable solvent. Alternatively, alkali metal salts of compounds of general formula (VI) may be isolated and converted into compounds of general formula (III) by treatment with a suitable reagent of general formula $R^2L$ in a suitable solvent, as a subsequent step. Compounds of general formula (VII) can be prepared by treatment of pyrroles of general formula (VIII) with a suitable base, such as sodium hydride or potassium tert-butoxide, and a substituted acetic ester of general formula $LCH_2CO_2R^1$, in a suitable solvent.

Alternatively, compounds of general formula (VII) may be prepared by treatment of the appropriately substituted dialkoxytetrahydrofuran of general formula (IX) with the glycine ester of general formula $H_2NCH_2CO_2R^1$ in a suitable solvent, for example, acetic acid, (see C. W. Jefford and W. Johncock, *Helvetica Chimica Acta*, 1983, 66, 2666).

*Chem. Soc., Chem. Commun.* 1980, 838, and references therein).

Acetals of general formula (X) may be prepared from pyrroleacetic esters of general formula (VII) by treatment of alkyl silyl ketene acetal derivatives of species (VII) with trialkylorthoformates of general formula $(R^2O)_3CH$ in the presence of a Lewis acid in a suitable solvent and at a suitable temperature (see, for example, K. Saigo, M. Osaki and T. Mukaiyama, *Chem. Letts.*, 1976, 769).

Compounds of general formula (I) in which V is sulphur may be obtained from thioethers corresponding to ethers of general formula (III), wherein $OR^2$ is replaced by $SR^2$, using the various processes shown in Schemes I and II. Thioethers corresponding to ethers of general formula (III), wherein $OR^2$ is replaced by $SR^2$, may be obtained by treating compounds of general formula (VI) with a suitable reagent of general formula $R^{19}SO_2Cl$, wherein $R^{19}$ is alkyl or optionally substituted aryl, in a suitable solvent and often in the presence of a base and then quenching with a reagent of general formula $NaSR^2$, wherein $R^2$ is defined above, e.g. sodium methanethiolate.

Moreover, compounds of formulae (IA), (IB), (IC), (ID) or (IE) may, where appropriate, be prepared from the appropriately substituted pyrrole of general formula (XI):

Scheme III

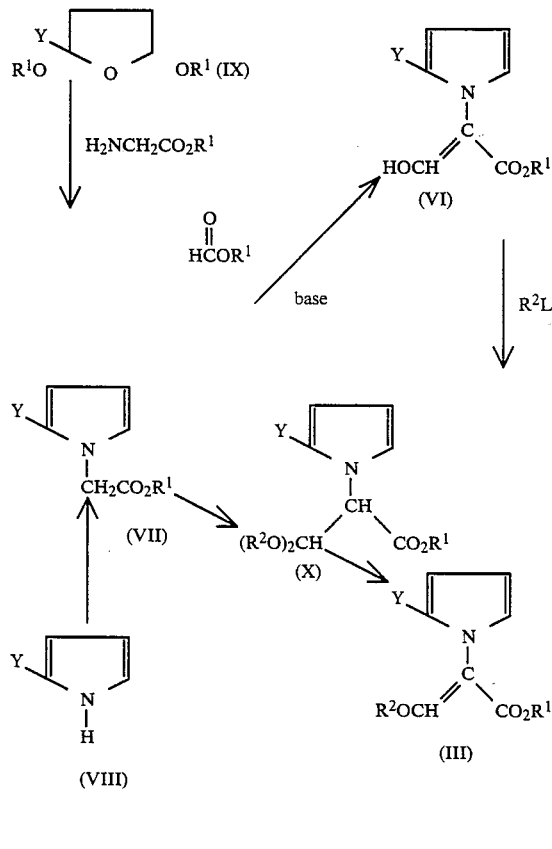

Furthermore, compounds of general formula (III) can be made from acetals of general formula (X) under either basic or acidic conditions, in suitable solvents and at suitable temperatures. An example of a suitable base is lithium di-isopropylamide, and potassium hydrogen sulphate is an example of a suitable acidic reagent (see T. Yamada, H. Hagiwara and H. Uda, *Journal of the*

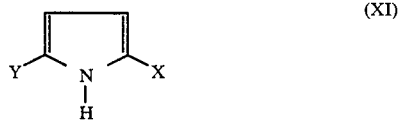

(XI)

via compounds of general formulae (XII), (XIII) and (XIV):

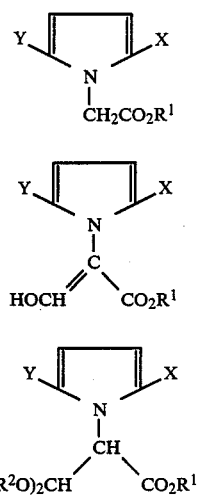

using the sequence outlined before in Scheme III to convert compounds of general formula (VIII) to compounds of general formula (III).

Compounds of general formulae (VIII), (IX) and (XI) may be prepared by methods known in the chemical literature.

In further aspects, the invention provides processes as herein described for preparing the compounds of the invention and the intermediate chemicals of formulae (IV), (V), (X) and (XII) to (XIV) used therein.

The compounds of the invention are active fungicides and may be used to control one or more of the following pathogens:

Pyricularia oryzae on rice.

*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines. Helminthosporium spp., Rhynchosporium spp., and Septoria spp. on cereals. Cercospora arachidicola and Cercosporidium personata on peanuts and other Cercospora species on other hosts for example sugar beet, bananas, soya beans and rice. *Botrytis cinerea* (grey mould) on tomatoes, strawberries, vegetables, vines and other hosts. Alternaria species on vegetables (e.g. cucumber), oil-seed rape, apples, tomatoes and other hosts. *Venturia inaequalis* (scab) on apples. *Plasmopara viticola* on vines. Other downy mildews such as *Bremia lactucae* on lettuce, Peronospora spp. on soybeans, tobacco, onions and other hosts and *Pseudoperonospora humuli* on hops and *Pseudoperonospora cubensis* on cucurbits.

*Phytophthora infestans* on potatoes and tomatoes and other Phytophthora spp. on vegetables, strawberries, avocado, pepper, ornamentals, tobacco, cocoa and other hosts.

Some of the compounds show a broad range of activities against fungi in vitro. They may also have activity against various post-harvest diseases of fruit (e.g. *Penicillium digitatum* and italicum and *Trichoderma viride* on oranges, *Gloeosporium musarum* on bananas and *Botrytis cinerea* on grapes).

Further some of the compounds may be active as seed dressings against Fusarium spp., Septoria spp., Tilletia spp., (bunt, a seed-borne disease of wheat), Ustilago spp. and Helminthosporium spp. on cereals and *Pyricularia oryzae* on rice.

The compounds may move acropetally in the plant tissue.

The invention therefore provides a method of combating fungi, which comprises applying to a plant, to a seed of a plant, or to the locus of the plant or seed, a fungicidally effective amount of a compound as hereinbefore defined, or a composition containing the same.

The compounds may also be useful as industrial (as opposed to agricultural) fungicides, e.g. in the prevention of fungal attack on wood, hides, leather and especially paint films.

Some of the compounds exhibit insecticidal activity and, at appropriate rates of application, may be used to combat a range of insect, nematode and mite pests.

Therefore in another aspect of the invention there is provided a method of killing or controlling insect, nematode and mite pests which comprises administering to the pest or to the locus thereof an insecticidally, nematocidally or miticidally effective amount of compound as hereinbefore defined or a composition containing the same.

Preferred compounds for use in this method are those of formula (II) in which Z is NOR$^5$ or C(A)B; R$^4$, Y and B are hydrogen; A is C$_{1-4}$ alkoxycarbonylmethyl; and R$^5$ is C$_{1-6}$ alkyl, C$_{2-6}$ alkenyl or C$_{2-6}$ alkynyl, and especially compounds 2, 3, 7 and 11 of Table I. Particularly preferred compounds for killing nematode pests are those of formula (II) in which Z is NOR$^5$; R$^4$, Y and B are hydrogen and R$^5$ is C$_{2-6}$ alkenyl, and especially compound 3 of Table I.

Some compounds exhibit plant growth regulating activity and may be deployed for this purpose, again at appropriate rates of application.

Therefore, in yet another aspect the invention provides a method of regulating plant growth which comprises applying to a plant, to a seed of a plant or to the locus of the plant or seed an effective amount of a compound as hereindefined or a composition containing the same. Preferred compounds for use in this method are those of formula (II).

The compounds may be used directly for agricultural purposes but are more conveniently formulated into compositions using a carrier or diluent. The invention thus provides fungicidal, plant growth regulator, insecticidal, nematicidal and miticidal compositions comprising a compound as hereinbefore defined, and an acceptable carrier or diluent therefor.

The compounds can be applied in a number of ways. For example they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or N,N-dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which plant possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl-aluminium, fenarimol, iprodione, prothiocarb, procymidone, vinclozolin, penconazole, myclobutanil, propamocarb, R0151297, diniconazole, pyrazophos, ethirimol, ditalimfos, tridemorph, triforine, nuarimol, triazbutyl, guazatine, triacetate salt of 1,1'-iminodi(octamethylene)diguanidine, buthiobate, propiconazole, prochloraz, flutriafol, hexaconazole, (2 RS, 3 RS)-2-(4-chlorophenyl)-3-cyclopropyl-1-(1H-1,2,4-triazol-1-yl)butan-2-ol, (RS)-1-(4-cholorophenyl)-4,4-dimethyl-3-(1H-1,2,4-triazol-1-ylmethyl)pentan-3-ol, fluzilazole, triadimefon, triadimenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, 4-chloro-N-(cyano(ethoxy)methyl)benzamide, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothal-isopropyl, dodine, dithianon, fentin hydroxide, fentin acetate, tecnazene, quintozene, dicloran, copper containing compounds such as copper oxychloride, copper sulphate and Bordeaux mixture, and organomercury compounds. The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (e.g. GA$_3$, GA$_4$ or GA$_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acid (e.g. triiodobenzoic acid), morphactins (e.g. chlorfluoroecol), maleic hydrazide, glyphosate, glyphosine, long chain fatty alcohols and acids, dikegulac, paclobutrazol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention. Throughout these examples, magnesium sulphate was used to dry solutions. Solutions were concentrated under reduced pressure, and reactions involving water sensitive intermediates were performed under an atmosphere of nitrogen. HPLC is high performance liquid chromatography; DMF is N,N-dimethylformamide; m.p. is melting point. Percentages are by weight.

EXAMPLE 1

This Example illustrates the preparation of the 2 geometric isomers of (Z)-methyl 3-methoxy-2-[2-(N-methoxyimino)pyrrol-1-yl]acrylate: Compounds 1 and 2 of Table 1.

A solution of the hydrochloride salt of the methyl ester of glycine (6.30 g) and potassium acetate (8.00 g) in water (10 ml) was added to glacial acetic acid (50 ml). The resulting mixture was heated to reflux, 2,5-dimethoxytetrahydrofuran (6.60 g) was added in one portion, and heating under reflux was continued for 4 hours. After cooling, the reaction mixture was neutralised with sodium bicarbonate and extracted with ethyl acetate. The extracts were washed with water, dried, concentrated under reduced pressure, and distilled at 125° C. and ca. 15 torr using a short-path distillation apparatus to give methyl pyrrol-1-ylacetate (2.62 g, 38% yield) as a colourless liquid, infrared (film) 1750 cm$^{-1}$.

A solution of methyl pyrrol-1-ylacetate (2.00 g) in methyl formate (4.4 ml) was added dropwise to a stirred suspension of sodium hydride (0.38 g) in dry toluene (10 ml) cooled in an ice bath. The mixture was allowed to warm to room temperature, 2 drops of dry methanol were added (effervescence), and it was heated slowly to 50° C. whereupon the mixture became at first clear, then deposited a thick off-white solid. The mixture was heated at 50° C. for 30 minutes, allowed to cool and diluted with ether. The solid was filtered off, washed with ether and partially dried to give a white solid (3.12 g) infrared (film) 1665, 1650 cm$^{-1}$. Methyl iodide (0.93 ml) was added in one portion to a stirred suspension of this solid in DMF (20 ml). After stirring at room temperature for 2 hours, the mixture was poured into water and extracted with ether. The extracts were washed with water, dried and concentrated to give a white solid (2.35 g) which was triturated with petrol and dried to give (Z)-methyl 3-methoxy-2-(pyrrol-1-yl)acrylate (1.73 g, 66%) as a white solid, m.p. 88°-9° C., infrared (nujol-mull) 1700, 1635 cm$^{-1}$, proton n.m.r. (CDCl$_3$) delta: 3.77 (3) s, 3.91 (3) s, 6.26 (2) t, 6.69 (2) t, 7.51 (1) s.

A solution of (Z)-methyl 3-methoxy-2-(pyrrol-1-yl)acrylate (10 g, 0.055 mol) in 1,2-dichloroethane (25 ml) was added dropwise with stirring at room temperature to the mixture resulting from adding phosphoryl chloride (5.6 ml, 0.06 mol) to DMF (4.7 ml, 0.06 mol) while cooling in ice. After stirring for 3 hours at room temperature, a saturated aqueous solution of sodium acetate (100 ml) was added and the resulting mixture was heated at reflux for 30 minutes. The mixture was cooled then extracted with dichloromethane (2×150 ml). The extracts were washed with water, dried and concentrated to give a clear oil (11.7 g, of a mixture of the 2 and 3-formylated pyrrole) which was purified by HPLC on silica gel using diethyl ether as the eluant to give (Z)-methyl 3-methoxy-2-(2-formylpyrrol-1-yl)acrylate (5.7 g, 45%) as a white crystalline solid, m.p. 58°-9° C., proton n.m.r. (CDCl₃) delta: 3.74 (3) s, 3.88 (3) s, 6.35 (1) m, 6.87 (1) m, 7.04 (1) m, 7.55 (1) s, 9.30 (1) d.

A mixture of the (Z)-methyl 3-methoxy-2-(2-formylpyrrol-1-yl)acrylate (0.5 g, 0.0024 mol), anhydrous sodium acetate (1.0 g, 0.012 mol) and methoxylamine hydrochloride (0.5 g, 0.006 mol) was refluxed in methanol for 3 hours. The resulting mixture was concentrated and the residue was partitioned between ethyl acetate (100 ml) and water (100 ml). The ethyl acetate layer was washed with brine, dried, concentrated and purified by HPLC on a column of silica gel using ether as the eluant to give:

(i) a clear oil (0.33 g, 57%), the (E)-isomer of the title compound (Compound 1 of Table I), which eluted first and, (ii) a clear oil (0.24 g, 42%) the (Z)-isomer of the title compound (Compound 2 of Table I), which eluted second.

EXAMPLE 2

This Example illustrates, with reference to Scheme IV, the preparation of (Z)-methyl 3-methoxy-2-[2-(E-2-carbethoxyethenyl)pyrrol-1-yl]acrylate (XII; Scheme IV): Compound 12 of Table I.

Referring to Scheme IV, a mixture of (Z)-methyl 3-methoxy-2-(2-formylpyrrol-1-yl)acrylate [1.0 g, 0.005 mol, (XIII); Scheme IV: preparation described in Example 1] and ethyl (triphenylphosphoranylidene)acetate (1.74 g, 0.005 mol) was refluxed in dry toluene (40 ml) for 30 hours. After cooling, the solution was concentrated and the residue was extracted with diethyl ether. These extracts were concentrated and then purified by HPLC on a column of silica gel using diethyl ether as the eluant, to give the title compound as a light orange oil (0.65 g, 47%).

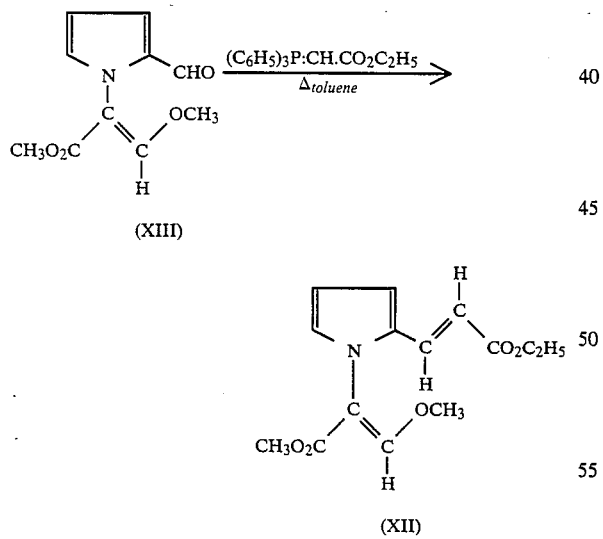

EXAMPLE 3

This Example illustrates the preparation of (Z)-methyl 3-methoxy-2-[2-(dimethylaminomethyl)pyrrol-1-yl]acrylate: Compound 1 of Table II.

Dimethylamine (5.4 g of a 33% aqueous solution, 0.04 mol) was added, with stirring, to glacial acetic acid (5 ml) whilst cooling in an ice bath; after 15 minutes formalin (3 mls of a 40% aqueous solution, 0.04 mol) was added and the mixture was stirred for 1 hour. (Z)-methyl 3-methoxy-2-(pyrrol-1-yl)acrylate (3.6 g, 0.02 mol, prepared as described in Example 1) was added and the mixture was stirred overnight. This was then concentrated and the residue was dissolved in water (100 ml). The resulting aqueous solution was washed with ether, neutralised with sodium bicarbonate, then extracted with ethyl acetate (2×80 ml). The extracts were dried and concentrated to give the title compound (3.75 g, 79%) as an oil which solidified on trituration with petrol 60°–80° C.; m.p. 54°–56° C.

EXAMPLE 4

This Example illustrates the preparation of the quaternary methiodide salt of (Z)-methyl 3-methoxy-2-[2-(dimethylaminomethyl)pyrrol-1-yl]acrylate: Compound 2 of Table II.

Iodomethane (0.53 ml, 0.0085 mol) was added to a solution of (Z)-methyl 3-methoxy-2-[2-(dimethylaminomethyl)pyrrol-1-yl]acrylate (1.9 g, 0.008 mol, prepared as described in Example 3) in chloroform (20 ml). This solution was kept at 0° C. for 16 hours, then concentrated and the residue was washed with ether to give the title compound (2.5 g, 85%) as a white crystalline solid, which did not melt on heating, but instead darkened at ca. 300° C.

EXAMPLE 5

An emulsifiable concentrate is made up by mixing and stirring the ingredients until all are dissolved.

| | |
|---|---|
| Compound No. 1 (Table II) | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 6

The active ingredient is dissolved in methylene dichloride and the resultant liquid sprayed onto granules of attapulgite clay. The solvent is then allowed to evaporate to produce a granular composition.

| | |
|---|---|
| Compound No. 1 (Table II) | 5% |
| Attapulgite granules | 95% |

EXAMPLE 7

A composition suitable for use as a seed dressing is prepared by grinding and mixing the three ingredients.

| | |
|---|---|
| Compound No. 1 (Table II) | 50% |
| Mineral oil | 2% |
| China clay | 48% |

EXAMPLE 8

A dustable powder is prepared by grinding and mixing the active ingredient with talc.

| | |
|---|---|
| Compound No. 1 (Table II) | 5% |

-continued

| | |
|---|---|
| Talc | 95% |

EXAMPLE 9

A suspension concentrate is prepared by ball milling the ingredients to form an aqueous suspension of the ground mixture with water.

| | |
|---|---|
| Compound No. 1 (Table II) | 40% |
| Sodium lignosulphonate | 10% |
| Bentonite clay | 1% |
| Water | 49% |

This formulation can be used as a spray by diluting into water or applied directly to seed.

EXAMPLE 10

A wettable powder formulation is made by mixing then grinding the ingredients until all thoroughly mixed.

| | |
|---|---|
| Compound No. 1 (Table II) | 25% |
| Sodium lauryl sulphate | 2% |
| Sodium lignosulphonate | 5% |
| Silica | 25% |
| China clay | 43% |

EXAMPLE 11

This Example illustrates the fungicidal properties of compounds 1 to 5, 7, 11, 12 and 19 of Table I and 5 of Table II when tested against a variety of foliar fungal diseases of plants. The technique employed was as follows.

The plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4=no disease
3=trace - 5% of disease on untreated plants
2=6-25% of disease on untreated plants
1=26-59% of disease on untreated plants
0=60-100% of disease on untreated plants
The results are shown in Table V.

TABLE V

| COMPOUND NO. | TABLE | PUCCINIA RECONDITA (Wheat) | ERYSIPHE GRAMINIS (Barley) | VENTURIA INAEQUALIS (Apple) | PYRICULARIA ORYZAE (Rice) | CERCOSPCRA ARACHIDICOLA (Peanut) | PLASMOPARA VITICOLA (Vine) | PHYTOPHTHORA INFESTANS (TOMATOES) |
|---|---|---|---|---|---|---|---|---|
| 1 | I | 4 | 4 | 4 | 4 | 4 | 4 | 3 |
| 2 | I | 4 | 4 | 4 | 3 | 4 | 4 | 0 |
| 3 | I | 4 | 4 | 4 | — | 4 | 4 | 0 |
| 4 | I | 4 | 4 | 4 | 4 | 4 | 4 | 4 |
| 5 | I | 3 | 3 | 4 | 4 | 3 | 4 | 0 |
| 7 | I | 4 | 4 | 4 | 4 | 4 | 4 | 3 |
| 11 | I | 4 | 4 | 4 | 4 | 2 | 4 | 4 |
| 12 | I | 4 | 0 | 4 | 4 | 4 | 4 | 4 |
| 19 | I | 4 | 0 | 0 | 0 | 3 | 4 | 0 |
| 5 | II | 2 | 2 | 4 | 0 | 4 | 0 | 0 |

EXAMPLE 12

This Example illustrates the plant growth regulating properties of compounds 1 to 5, 7, 11 and 12 of Table I when tested on a whole plant screen against various plant species. The plant species are identified in Table VI with the leaf stage at which they were sprayed.

A formulation of each chemical was applied at 4000 ppm (4 kg/ha in a 1000 l/ha field volume) using a track-sprayer and a SS8004E (Teejet) nozzle.

After spraying, the plants were grown in a glasshouse with 25° C. day/22° C. night temperatures. Supplementary lighting was supplied when necessary to provide an average photoperiod of 16 hours (14 hours minimum).

After 2-6 weeks in the glasshouse, depending on species and time of year, the plants were visually assessed for morphological characteristics against a control plant sprayed with a blank formulation. The results are presented in Table VII.

TABLE VI

| PLANT MATERIAL USED FOR WHOLE PLANT SCREEN | | | | | |
|---|---|---|---|---|---|
| Species | Code | Variety | Growth Stage at Treatment | No Plants per 3" pot | Compost Type |
| Barley | BR | Atem | 1-1.5 leaves | 4 | JIP* |
| Maize | MZ | Earliking | 2¼-2½ leaves | 1 | PEAT |
| Apple | AP | Red Delicious | 4-5 leaves | 1 | JIP |

TABLE VI-continued

PLANT MATERIAL USED FOR WHOLE PLANT SCREEN

| Species | Code | Variety | Growth Stage at Treatment | No Plants per 3" pot | Compost Type |
|---|---|---|---|---|---|
| Rice | RC | Ishikari | 2-2½ leaves | 4 | JIP |
| Tomato | TO | Ailsa Craig | 2-2½ leaves | 1 | PEAT |

*John Innes Potting Compost

TABLE VII

| Plant Material | Compound No. | R | G | A | T | I | P |
|---|---|---|---|---|---|---|---|
| BR | 3 | | | | | | |
| BR | 4 | | | | | | |
| BR | 5 | | | | | | |
| BR | 11 | | | | | 1 | 1 |
| RC | 3 | | | | | 1 | |
| RC | 4 | | 1 | | | | |
| RC | 5 | | | | | | |
| RC | 11 | 1 | | | | 1 | |
| AP | 3 | | | | | | |
| AP | 4 | 2 | | | | 2 | |
| AP | 5 | 2 | | | | 2 | |
| AP | 11 | 1 | | | | 1 | |
| TO | 3 | 3 | | 3 | | | 3 |
| TO | 5 | 3 | | 3 | | | 3 |
| TO | 7 | 2 | | 3 | 2 | 2 | 2 |
| TO | 11 | 3 | | 3 | 1 | | 3 |
| TO | 12 | 3 | | 3 | | 3 | 3 |
| MZ | 1 | 1 | | | | 2 | |
| MZ | 2 | | | | | | |
| MZ | 3 | 1 | | 3 | | | |
| MZ | 4 | | | 1 | | | |
| MZ | 5 | | | | | | |
| MZ | 7 | 1 | | | | | |
| MZ | 11 | 1 | | | | | |
| MZ | 12 | 2 | 1 | | | 3 | |

KEY
R = Retardation
G = Greening effect
A = Apical damage
T = Tillering or side shooting
I = Interligular of internodal length reduction
P = Phytotoxicity
All effects, except phytotoxicity, are scored visually on a 1-3 basis where
1 = 10-30%
2 = 31-60%
3 = 61-100%
Blank means less than 10% effect.
Phytotoxicity is scored on a 1-5 basis where
1 = less than 10%
2 = 11-30%
3 = 31-50%
4 = 51-70%
5 = greater than 70%
Blank means no effect at all observed.

EXAMPLE 13

This Example illustrates the insecticidal properties of compounds 2, 3, 7 and 11 of Table I.

The activity of the compounds was determined using a variety of insect, mite and nematode pests. The compounds were used in the form of liquid preparations containing 500 parts per million (ppm) by weight of the compound except for the test on *Meloidogyne incognita* when liquid preparations of 250 ppm by weight were used. The preparations were made by dissolving the compounds in acetone and diluting the solutions with water containing 0.1% by weight of a wetting agent sold under the trade name "SYNPERONIC" NX until the liquid preparations contained the required concentration of the product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to seven days after the treatment.

The results of the tests are given in Table IX for each of the products as a grading of mortality designated as 9, 5 or 0 where 9 indicates 80-100% mortality (70-100% root-knot reduction as compared with untreated plants for *Meloidogyne incognita*), 5 indicates 50-79% mortality (50-69% root knot reduction for *Meloidogyne incognita*) and 0 indicates less than 50% mortality (root-knot reduction for *Meloidogyne incognita*).

In Table IX the pest organism used in designated by a letter code and the pests species, the support medium or food, and the type and duration of test is given in Table VII.

TABLE VII

| CODE LETTERS (Table IV) | TEST SPECIES | SUPPORT MEDIUM/ FOOD | TYPE OF PEST | DAY |
|---|---|---|---|---|
| TUa | *Tetranychus urticae* (spider mites - adult) | French bean leaf | Contact | 3 |
| TUe | *Tetranyhus urticae* (spider mites - ova) | French bean leaf | Contact | 6 |
| MP | *Myzus persicae* (aphids) | Chinese Cabbage leaf | Contact | 3 |
| NL | *Nilaparvata lugens* (brown plant hopper - nymphs) | Rice plant | Contact | 3 |
| HV | *Heliothis virescens* (tobacco budworm - larvae) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Cotton wool/ sugar | Contact | 1 |
| SP | *Spodoptera exigua* (lesser army worm - larvae) | Cotton leaf | Residual | 3 |
| MI | *Meloidogyne incognita* (tomato root knot eelworm - larvae) | Semi in-vitro | Residual | 7 |
| NC | *Nephotettix cincticeps* (green leaf hopper - nymph) | Rice plant | Contact | 3 |

TABLE VII

| COMPOUND NO. | TU$_a$ | TU$_e$ | MP | NL | MD | BG | HV | SP | DB | MI | NC |
|---|---|---|---|---|---|---|---|---|---|---|---|
| 2 | 9 | 0 | 9 | 0 | 0 | 0 | 0 | 0 | 5 | 0 | — |
| 3 | 9 | 0 | 0 | 9 | 9 | 9 | 0 | 0 | 9 | 5 | — |
| 7 | 9 | 0 | 0 | 0 | 0 | 5 | — | — | 9 | 0 | — |

TABLE VII-continued

| COMPOUND NO. | $TU_a$ | $TU_e$ | MP | NL | MD | BG | HV | SP | DB | MI | NC |
|---|---|---|---|---|---|---|---|---|---|---|---|
| 11 | 9 | 0 | 0 | — | 0 | 9 | 0 | — | 0 | 0 | 5 |

The knockdown properties of compound 3 in Table I against *Musca domestica* were demonstrated as follows.

A sample of compound 3 was diluted in 2 mls acetone and made upto a 2000 ppm solution with 0.1% aqueous synperonic solution. The solution (1 ml) was then sprayed directly onto twenty mixed sex houseflies held in a drinking cup. Immediately after spraying the cups were inverted and left to dry. An assessment of knockdown was made when the cups were righted 15 minutes later. The flies were then provided with a 10% sucrose solution on a cotton wool pad, and held for 48 hours in a holding room conditioned at 25° C. and 65% relative humidity before a mortality assessment was made.

Compound 3 in Table I under these conditions demonstrated 90% knockdown and 93% kill.

We claim:

1. A compound of formula (I):

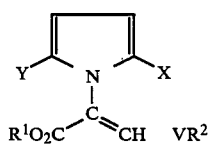

and stereoisomers and salts thereof, wherein $R^1$ and $R^2$, which are the same or different, are $C_{1-6}$ alkyl; V is oxygen or sulphur; Y is hydrogen, $C_{1-6}$ alkyl, cyano, nitro or halogen; X is

Z is $NOR^5$ or

A is $CO_2R^6$, $COR^7$, cyano, nitro or acylamino; B is hydrogen, $C_{1-6}$ alkyl, phenyl, $CO_2R^8$, $COR^9$, cyano, nitro or acylamino; $R^4$ is $CO_2R^3$ or $R^{17}$; $R^3$ is $C_{1-6}$ alkyl; $R^5$ to $R^9$ and $R^{17}$, which are the same or different, are hydrogen, $C_{1-6}$ alkyl, $C_{3-6}$ cycloalkyl, $C_{3-8}$ cycloalkyl-($C_{1-6}$)alkyl, $C_{2-6}$ alkenyl, $C_{2-6}$ alkynyl, phenyl or phenyl($C_{1-6}$)alkyl; any alkyl, cycloalkyl or cycloalkylalkyl moiety being unsubstituted or substituted with hydroxy, halogen, $C_{1-4}$ alkoxy or $C_{1-4}$ alkoxycarbonyl, any alkynyl or alkenyl moeity being unsubstituted or substituted with phenyl, and any phenyl being unsubstituted or substituted with halogen, hydroxy, $C_{1-6}$ alkyl, methoxy, trifluoromethyl or trifluoromethoxy.

2. A fungicidal composition comprising as an active ingredient a compound according to claim 1 and a fungicidally acceptable carrier or diluent therefor.

3. A method of combating fungi which comprises applying to a plant, to seed of a plant or to the locus of the plant or seed, a compound according to claim 1.

4. A compound according to claim 1 wherein $R^1$ and $R^2$ are methyl, V is oxygen, $R^4$ is hydrogen, $C_{1-6}$ alkyl or phenyl and $R^5$ is hydrogen, $C_{1-6}$ alkyl, $C_{2-6}$ alkynyl, $C_{2-6}$ alkynyl, phenyl or phenyl($C_{1-4}$)alkyl.

* * * * *